United States Patent [19]
Harrison

[11] 3,965,157
[45] June 22, 1976

[54] PREPARATION OF α-ACETOXY ALDEHYDES AND KETONES

[75] Inventor: Roger Garrick Harrison, Hampshire, England

[73] Assignee: Lilly Industries, Ltd., England

[22] Filed: Dec. 16, 1974

[21] Appl. No.: 533,358

[30] Foreign Application Priority Data
Dec. 17, 1973 United Kingdom............ 58352/73

[52] U.S. Cl.......................... 260/491; 260/327 M
[51] Int. Cl.²........................................ C07C 67/28
[58] Field of Search...... 260/488 R, 488 CD, 488 F, 260/491

[56] References Cited
UNITED STATES PATENTS

| | | | |
|---|---|---|---|
| 2,156,721 | 5/1939 | Simo et al. | 260/488 F |
| 2,198,172 | 4/1940 | McGill | 260/488 F |
| 2,726,260 | 12/1955 | Novello | 260/488 CD |
| 2,834,792 | 5/1958 | Wilkinson, Jr. et al. | 260/491 |
| 2,892,865 | 6/1959 | Giraldi et al. | 260/488 CD |

*Primary Examiner*—Vivian Garner
*Attorney, Agent, or Firm*—Charles W. Ashbrook; Everet F. Smith

[57] ABSTRACT

An improved method for the preparation of intermediates of formula:

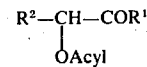

where $R^1$ and $R^2$ represent hydrogen, $C_{1-4}$ alkyl, $C_{1-4}$ hydroxyalkyl, $C_{3-10}$ cycloalkyl, $C_{3-6}$ acyloxyalkyl, or phenyl, by mercuric ion assisted hydrolysis of the corresponding dithianes, and novel intermediates thereby produced.

8 Claims, No Drawings

PREPARATION OF α-ACETOXY ALDEHYDES AND KETONES

The present invention relates to an improved process for preparing α-acyloxy ketones and aldehydes which are useful as intermediates in the preparation of pharmacologically-active oxazole derivatives.

In the specification of Neville and Verge's co-pending U.S. application Ser. No. 533,417 filed this even date herewith, there is described inter alia a process for preparing pharmacologically-active N,N-di-substituted amino-4-$R^1$-substituted 5-$R^2$-substituted oxazoles, useful as anti-asthma agents, which process includes the step of reacting a compound of the formula:

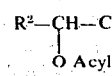
I with cyanamide or a mono-substituted cyanamide. The present invention is concerned with providing an improved process for preparing compounds of formula I in which $R^1$ and $R^2$ are independently hydrogen, $C_{1-4}$ alkyl, $C_{1-4}$ hydroxyalkyl, $C_{3-10}$ cycloalkyl, $C_{3-6}$ acyloxyalkyl or an optionally substituted phenyl group.

According to the present invention, there is provided a process for preparing a compound of formula I, which comprises the hydrolysis of a compound of formula:

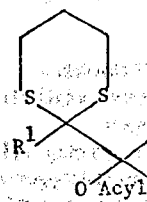
IV in the presence of mercuric ion to produce the desired compound of formula I.

Preferably, the compound of formula IV is prepared by the steps of:

i. reacting an aldehyde of formula $R^2CHO$ with a 2-lithio-1,3-dithiane of formula:

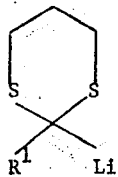
II ii. acylating the resultant compound of formula:

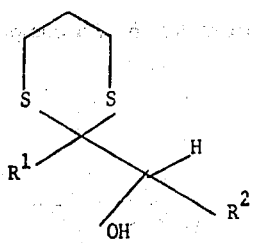
III to form the compound of formula IV.

The lithio dithiane of formula II used in step (i) may be prepared by reacting the appropriate 2-$R^1$-substituted-1,3-dithiane with an alkyl lithium such as n-butyl lithium. The reaction is normally carried out at low temperature, for example −20° to −40°C., and in an appropriate solvent such as tetrahydrofuran, hexane or a mixture thereof. The reaction is usually complete within 1 to 2 hours.

In step (i), the aldehyde $R^2CHO$ (dissolved in a solvent such as tetrahydrofuran) is added slowly to a solution of the lithio dithiane at a temperature of −20° to −40°C., the latter preferably being in situ in the reaction medium in which it was formed, and the temperature allowed to rise to room temperature over a period of from 1 to 16 hours.

Step (ii) involves conventional acylation of the resultant compound from step (i). The acylating agent used is not critical to the process of the invention since, in the intended use of the compounds of formula I as outlined above, the acyl function is eliminated during the subsequent reaction with cyanamide or a mono-substituted cyanamide. For convenience only therefore, the acylating agent normally used in step (ii) is acetic anhydride, the acylation usually being carried out at ambient temperature in a suitable solvent such as pyridine and being complete within about 16 hours. On completion of the reaction, removal of the solvent and any excess acylating agent yields the desired compound of formula IV.

As described above, the resultant dithioacetal of formula IV is hydrolysed to the desired compound of formula I by hydrolysis in the presence of mercuric ion. Any appropriate source of the latter ion may be used but preferably the source is mercuric chloride.

In a preferred hydrolysis according to the present invention, a solution of the compound of formula IV in a solvent such as acetonitrile is added to a stirred suspension of mercuric chloride/cadmium carbonate in acetonitrile/water and the mixture is agitated at 50° to 60°C. under an inert gas atmosphere such as nitrogen for up to 36 hours. The resultant compound of formula I may be isolated by removal of the solvent, extraction of the residue with, for example, benzene/chloroform, evaporation of the extract and distillation of the resultant residue.

As used above, the term "$C_{1-4}$ alkyl" means a straight or branched chain alkyl group containing from 1 to 4 carbon atoms such as methyl, ethyl, isopropyl, n-butyl, isobutyl and t-butyl. "$C_{1-4}$ hydroxyalkyl" and "$C_{3-6}$ acyloxyalkyl" mean the aforementioned $C_{1-4}$ alkyl groups substituted by a hydroxy and acyloxy group respectively. "$C_{3-10}$ cycloalkyl" means a saturated ring having from 3 to 10 carbon atoms in the ring such as cyclopropyl, cyclobutyl, cyclohexyl, cyclooctyl, or adamantyl. The term "optionally substituted phenyl" means a phenyl group unsubstituted or substituted by one or more groups such as halogen, trifluoromethyl, methyl, methoxy or nitro.

Preferably, $R^1$ and $R^2$ independently represent hydrogen or $C_{1-4}$ alkyl. However, if one or other of $R^1$ and $R^2$ represent a $C_{3-10}$ cycloalkyl group, it is preferred that the cycloalkyl group contains 8 or less carbon atoms.

The reaction of the invention is particularly useful when $R^2$ is hydrogen since, heretofore, compounds of this type have been particularly difficult to prepare.

Compounds of formula I in which $R^2$ is hydrogen when $R^1$ is hydrogen or $C_{1-4}$ alkyl are known. All other compounds of formula I are novel and are provided in a further aspect of the invention.

The following Examples will further illustrate the improved process of the present invention:

EXAMPLE 1

1,3-Dithiane (5 g.) in dry tetrahydrofuran (50 ml.) was cooled to −30°C. during the addition of one equivalent of a solution of n-butyl lithium in hexane. After a further 1 hour at −30°C., cyclohexyl carboxaldehyde (4.7 g.) in tetrahydrofuran (10 ml.) was added slowly. The temperature was allowed to rise to 20°C. over 2 hours and then water was added and the product isolated in ether. Removal of solvent in vacuo gave an oil which crystallised from ether/petrol (b.p. 40° to 60°C.), 6.8g (70%), m.p. 64° to 65°C.

Analysis: $C_{11}H_{20}S_2O$: Requires: C, 56.95; H, 8.69; S, 27.64%. Found: C, 57.1; H, 8.9; S, 27.35%.

The resultant 2-cyclohexyl-2-hydroxyacetaldehyde dithiane (6.8 g.) was converted into 2-cyclohexyl-2-acetoxyacetaldehyde dithiane using excess acetic anhydride in pyridine at ambient temperature for 16 hours. Removal of solvent and excess reagent in vacuo gave an oil which crystallised as white prisms from petrol (40° to 60°C.), 6.7 g. (85%), m.p. 84° to 85°C.

Analysis: $C_{13}H_{22}O_2S_2$: Requires: C, 57.0; H, 8.1; S, 23.4%. Found: C, 57.1; H, 7.8; S, 23.1%.

The 2-cyclohexyl-2-acetoxyacetaldehyde dithiane (6.0 g.) in acetonitrile (300 ml.) was added to a stirred suspension of mercuric chloride (19.2 g.) and cadmium carbonate (11.6 g.) in acetonitrile (200 ml.) and water (4 ml.). The mixture was then stirred at 50° to 60°C. under nitrogen for 36 hours. The acetonitrile was removed in vacuo and the residue was washed several times with benzene and once with chloroform. Evaporation of the solvent and distillation of the residue gave 2-cyclohexyl-2-acetoxyacetaldehyde as a colourless oil, b.p. 120°C. (air bath)/0.5 mm., 3.9 g. (95%).

Analysis: $C_{10}H_{16}O_3$: Requires: C, 65.3; H, 8.75%. Found: C, 65.2; H, 8.7%.

EXAMPLE 2

2-Cyclohexyl-1,3-dithiane (26 g.) in dry T.H.F. (200 ml.) was cooled to −30°C. and one equivalent of n-butyl lithium in hexane was added. Stirring was continued for a further 2 hours at −30°C., and then paraformaldehyde (4 g.) was added in portions. The solution was stirred for a further 13 hours as the temperature rose to 20°C. Water was then added and the product was isolated in ether. Evaporation of the solvent gave a colourless oil (31 g.).

The crude product from above (30 g.) in dry pyridine (100 c.c.) was acetylated with acetic anhydride at room temperature for 13 hours. Removal of solvent and excess reagent in vacuo gave an oil which was distilled at 138° to 141°C./1 mm., 18.8 g.

The resultant 2-cyclohexyl-2-acetoxymethyl-1,3-dithiane (18.5 g.) in acetonitrile (400 ml.) and water (10 ml.) was added to a suspension of mercuric chloride (38.4 g.) and cadmium carbonate (23 g.) in acetonitrile (200 ml.). The mixture was then heated at 50°C. under nitrogen for 30 hours. Solvent was then removed in vacuo and the residue was washed with benzene and chloroform. Evaporation of the extract followed by distillation at 150°C. (air-bath)/0.5 mm. gave 2-acetoxyacetylcyclohexane 9.7 g. (78%), m.p. 32° to 34°C.

Analysis: $C_{10}H_{16}O_3$: Requires: C, 65.3; H, 8.75%. Found: C, 65.0; H 8.85%.

Similarly, the following compounds were prepared:
1-acetoxy-2-butanone, b.p. 56° to 58°C./2 mm.
1-acetoxy-2-hexanone, b.p. 60°–65°C./1.5 mm. (m.p. ca. 28° to 30°C.)
1-acetoxy-3-methyl-2-butanone, b.p. 110°C.*/5 mm.

\* Air-bath temperature

I claim:

1. A process of preparing a compound of the formula

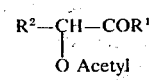

where $R^1$ and $R^2$ are independently hydrogen, $C_{1-4}$ alkyl, $C_{3-10}$ cycloalkyl, acetoxyalkyl wherein the alkyl group has 1–4 carbon atoms, phenyl, or phenyl substituted with one or more groups selected from halogen, methyl, trifluoromethyl, methoxy and nitro; which comprises hydrolyzing a compound of the formula:

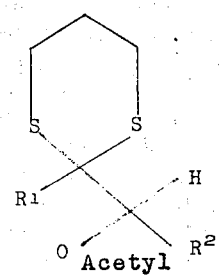

in the presence of mercuric ion.

2. A process according to claim 1, wherein $R^1$ is $C_{1-4}$ alkyl, and $R^2$ is hydrogen.

3. A process according to claim 1 wherein $R^1$ and $R^2$ independently represent hydrogen or $C_{1-4}$ alkyl.

4. A process according to claim 1 wherein the source of mercuric ion is mercuric chloride.

5. A process according to claim 1 wherein the hydrolysis is carried out under an inert gas atmosphere.

6. A process according to claim 1 wherein acetonitrile is used as solvent.

7. A process according to claim 1 wherein the compound of the formula

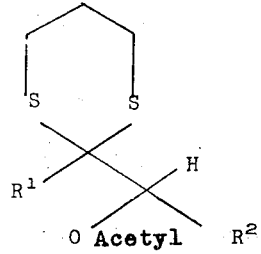

is prepared by acetylation of a compound of the formula

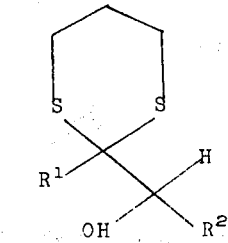

[III]

8. A process according to claim 7, wherein the compound of the formula
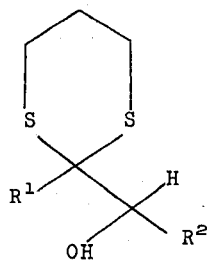
is prepared by reacting an aldehyde of the formula $R^2$ CHO with a 2-lithio-1,3-dithiane of the formula:
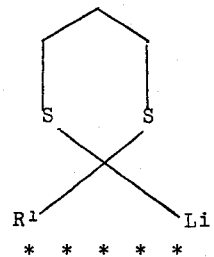
* * * * *